(12) United States Patent
Garito et al.

(10) Patent No.: US 6,926,717 B1
(45) Date of Patent: Aug. 9, 2005

(54) ELECTROSURGICAL BREAST ELECTRODE

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 74 days.

(21) Appl. No.: 10/341,087

(22) Filed: Jan. 14, 2003

(51) Int. Cl.[7] ............................................. A61B 18/18
(52) U.S. Cl. ......................................... 606/51; 606/52
(58) Field of Search ........................... 606/51, 52, 205, 606/206, 207; 128/898

(56) References Cited

U.S. PATENT DOCUMENTS

| | | | |
|---|---|---|---|
| 3,916,909 A * | 11/1975 | Kletschka et al. | 604/35 |
| 6,059,734 A * | 5/2000 | Yoon | 600/565 |
| 6,228,084 B1 * | 5/2001 | Kirwan, Jr. | 606/52 |
| 6,546,935 B2 * | 4/2003 | Hooven | 128/898 |
| 6,613,048 B2 * | 9/2003 | Mulier et al. | 606/49 |
| 6,679,881 B1 * | 1/2004 | Bybee | 606/51 |

* cited by examiner

*Primary Examiner*—Rosiland Rollins

(57) ABSTRACT

An electrosurgical electrode configured for use in a breast plastic surgical procedure comprises an elongated forceps that is operated as a unipolar electrode. The electrosurgical electrode is provided with internal channels that can provide suction or fluids at the surgical site when a source of suction or fluid is connected to the electrode. It is provided with uniquely configured cutting edges at its distal end for cutting tissue while simultaneously coagulating any bleeding that occurs. It can cleanly and precisely cut tissue and coagulate bleeding vessels at the same time.

16 Claims, 3 Drawing Sheets

ELECTROSURGICAL BREAST ELECTRODE

This invention relates to electrosurgery, and in particular to an electrode especially configured for surgery on the breast of a patient.

BACKGROUND OF THE INVENTION

Electrosurgery is a common procedure for dentists, doctors, and veterinarians. Electrosurgical handpieces are commercially available that will accommodate a wide variety of electrodes shapes and sizes, such as needles, blades, scalpels, balls and wire loops. Also, multi-function electrodes are available. A suction coagulator is described in U.S. Pat. No. 5,196,007, whose contents are herein incorporated by reference. This is an instrument that can be connected to a source of electrosurgical energy and that provides the handpiece in the form of a hollow tube with an exposed tip. By connecting a suction source to the hollow tube end, blood and other liquids as well as vapors and odors at the operative field can be drawn out while simultaneously bleeding capillaries can be coagulated electrosurgically.

The importance of using suction to capture smoke and plume generated during an electrosurgical procedure is also well known in the art. Such procedures involving tissue excision invariably result in the generation of smoke and odors. This causes several problems. Firstly, the smoke interferes with the vision of the surgeon. Secondly, the smoke can be inhaled by the patient or the surgeon. Thirdly, the odors are offensive. See, for example, U.S. Pat. No. 6,001,077, which describes a plume evacuation system employing a novel wand—the fitting used to capture the plume and which is attached to the suction apparatus—whose contents are herein incorporated by reference.

Reconstructive plastic surgery on the breast of a patient, especially breast implants, is a common surgical procedure. See for example the discussion and techniques described in RECONSTRUCTIVE PLASTIC SURGERY, $2^{nd}$ ed., Vol. 7, Pgs. 3689–3704, publ. By W.B. Saunders Company. One of the more important steps in performing a successful breast implant is creating the pocket for the implant. Traditionally, the pocket is created using a sharp instrument (scalpel or scissors) to cut and dissect the tissue. The main problem of creating the pocket with a sharp instrument is the bleeding which obscures the surgical site and can reduce the surgeon's accuracy. Bleeding is messy and time consuming to control but if time is not taken to control the bleeding, accuracy is compromised.

Another traditional method used to create the pocket is blunt dissection. Blunt dissection however can tear rather than precisely and cleanly cut the tissue. Tearing and separating tissue with blunt dissection is a blind method and while it is fast it is very traumatic and causes an abundance of bleeding.

While the two traditional methods are easy and fast to learn, the sharp or blunt dissection techniques cause more bleeding and more tissue injury, can tear tissue, and often result in a longer recovery time.

SUMMARY OF THE INVENTION

An object of the invention is an electrosurgical electrode for performing breast surgery causing fewer problems than known procedures.

A further object of the invention is an electrosurgical electrode that ensures that the active end from which suction is active is located close to the operative field.

Another object of the invention is a unipolar electrosurgical electrode configured to carefully dissect and coagulate breast tissue in a breast plastic surgical procedure.

Still a further object of the invention is a suction device integrated with an electrosurgical electrode specifically adapted for use in breast implantology.

In accordance with an important aspect of the present invention, an electrosurgical electrode configured for use in a breast plastic surgical procedure comprises an elongated forceps that is operated as a unipolar electrode.

In accordance with another aspect of the present invention, the electrosurgical electrode is provided with internal channels that can provide suction or fluids at the surgical site when a source of suction or fluid is connected to the electrode.

In accordance with still another aspect of the present invention, the electrosurgical electrode is provided with uniquely configured cutting edges at its distal end for cutting tissue while simultaneously coagulating any bleeding that occurs.

The unipolar electrosurgical forceps of the invention cleanly and precisely cuts tissue and coagulates bleeding vessels at the same time. It becomes possible to produce a very precise pocket in a relatively short time (less than 20–30 min). The result in a procedure for forming a pocket in the breast is a dry pocket, which means more accuracy and better vision for the surgeon. A shorter recovery time is possible for many augmentation patients. Even in submuscular pocket dissection, it is possible for the majority of the patients to return to normal life in less than two-three days.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

U.S. Pat. No. 6,001,077 shows a typical surgical smoke plume evacuation system with a hand-held wand connected via filters and a vacuum hose to a vacuum blower, referred to herein as the suction generator.

The invention described in the present application provides an electrode configuration that is stand alone, meaning that it incorporates the handpiece and is not attached to a standard handpiece as is more common in this art.

Figure 1:
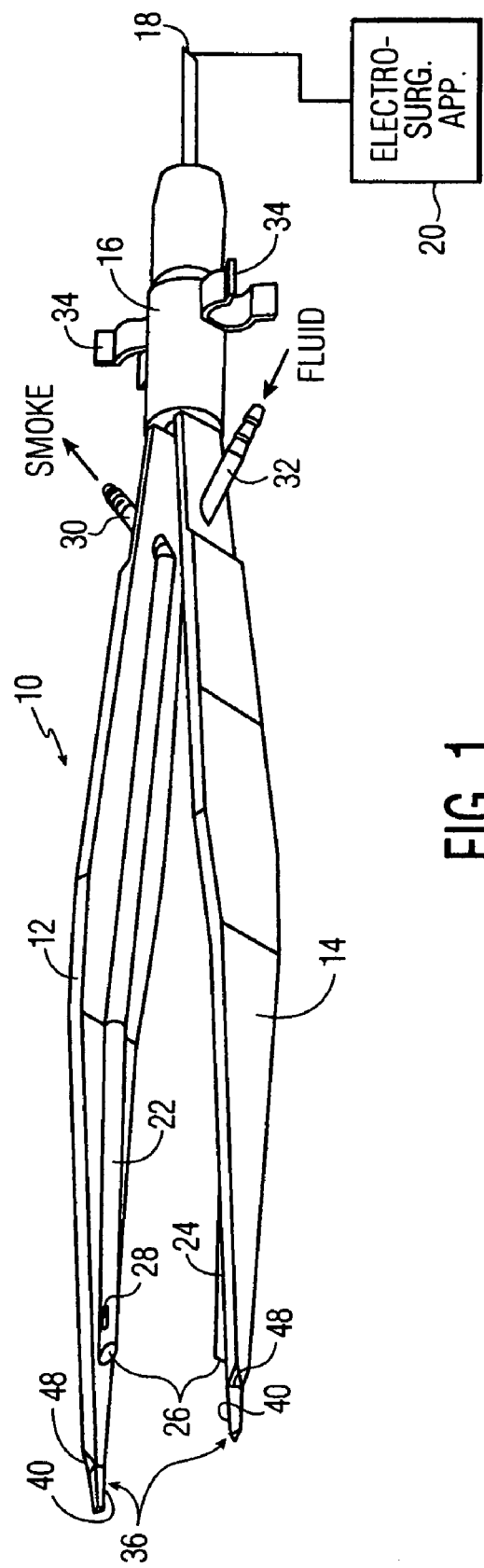
FIG. 1 is a perspective view of one form of electrosurgical electrode according to the invention shown electrically connected to electrosurgical apparatus and suction and fluid sources.
Figure 2:
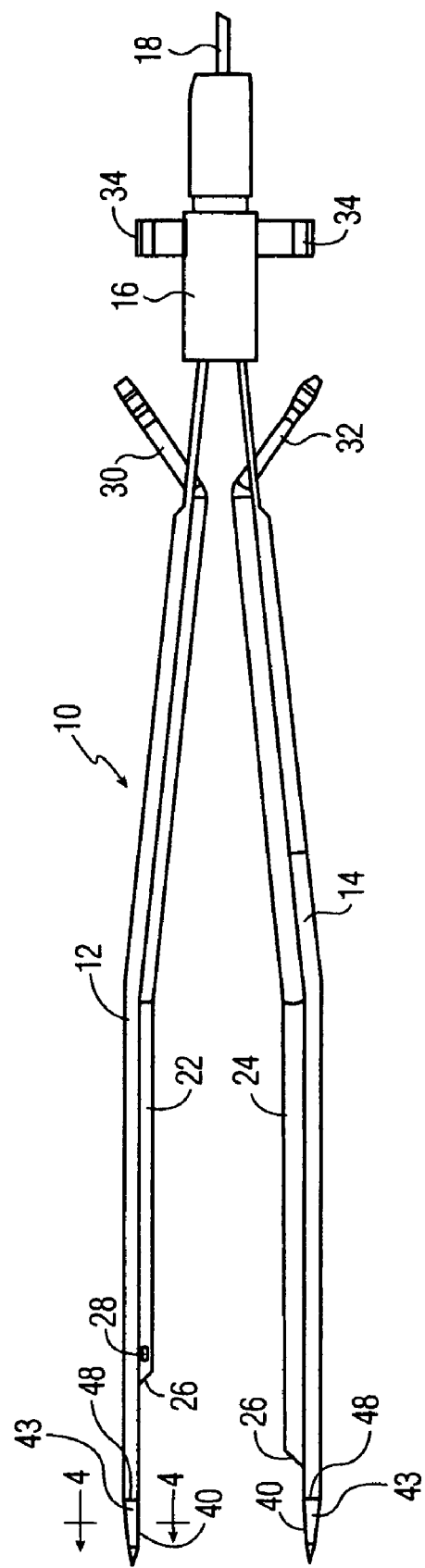
FIG. 2 is a top view of the electrosurgical electrode of FIG. 1.

FIG. 1 is a perspective view and FIG. 2 is a top view of a unipolar electrosurgical electrode 10 according to the invention. It is made of any electrically-conductive material preferably metal, e.g., stainless steel. It is completely coated with electrically-insulating material, except for the distal working end (explained below), and thus is configured to be handled by the surgeon, with the surgeon holding both arms 12, 14 of the forceps configuration in the palm of his hand. The two arms 12, 14 are attached at the proximal end to a common support 16 and are each configured so that they are biased outwardly, like ordinary forceps, so that when the surgeon release his or her pressure on the forceps' arms, they automatically assume the rest position shown in FIG. 2. The common metal support 16 is in turn connected to an electrical cable 18 connected at its opposite end to a connector (not shown) for plugging into a standard electrosurgical apparatus 20 supplying electrosurgical currents to the electrode 10. In this embodiment, the surgeon would use the standard foot pedal for activating and inactivating the apparatus 20. While not shown, it is possible to add to the forceps the kind of fingerswitches commonly found on electrosurgical handpieces to operate the apparatus 20.

The electrosurgical apparatus 20 preferably is a high frequency (RF) radiosurgical energy source, which operates in the range of about 3.8–4.0 MHz. Studies have shown that the 3.8–4.0 MHz frequency range is the preferred RF energy to incise and coagulate tissue because tissue thermal necrosis is minimal and, when interfaced with the electrosurgical electrode of the invention, provides excellent cutting and hemostasis for virtually all procedures. An example of suitable electrosurgical apparatus is the Model SUR-GITRON Dual-Frequency electrosurgical unit manufactured by and available from Ellman International, Inc. of Hewlett, N.Y.

Figure 3:
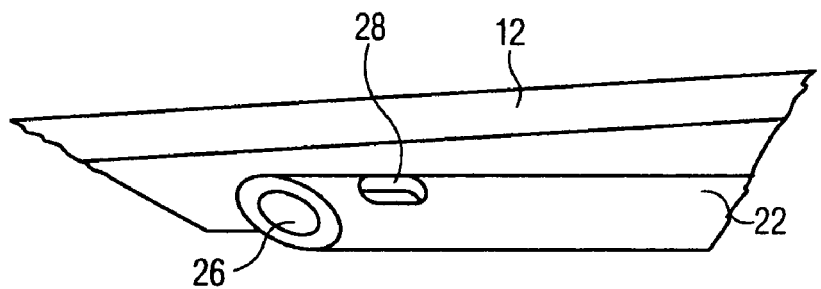
FIG. 3 is a perspective view of part of the front end of the electrosurgical electrode of FIG. 2.

Mounted along the inside of each of the forceps' arms 12, 14 are conduits in the form of narrow tubes 22, 24. The distal ends of the tubes 22, 24 are open 26. In addition, one of the tubes 22 has an additional opening 28 at the side near the end opening 26. Each of the tubes 22, 24 extend along the inside of their respective arm, pass through a an opening at the proximal arm end and terminate in fittings 30, 32 for receiving flexible tubes (not shown) which under normal operation would be respectively connected to a source of suction and fluid. The suction withdraws smoke at the surgical site and the fluid can be used by the surgeon for irrigating the surgical site, as illustrated by the arrows in FIG. 1. Fittings 34 are mounted on the common support 16 and are used to support the suction/fluid tubes, respectively. FIG. 3 is an enlarged view of the tube 22 on arm 12 showing the openings 26, 28.

Figure 4A:
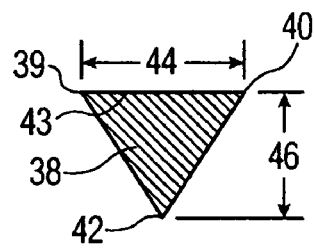
FIGS. 4A, 4B, and 4C cross-sectional views of the electrosurgical electrode of FIG. 2 along the lines 4—4.

At the distal end of each arm is located the working end 36 of the electrode 10. The working end comprises in this embodiment a short bare metal end that has a triangular configuration with triangle vertices 40 facing inward (and vertices 42 facing downward in the FIG. 2 view) to form on each forceps end a sharp cutter 38 with a flat top 43. The cutters 38 may have the same configuration. FIG. 4A is a cross-section at the working end and shows the triangular shape 38. When the forceps' arms are brought together, the vertices 40 on opposite corners abut. Thus, cutting can take place by bringing the forceps arms together using the inner vertices 40 to cut tissue between the forceps' ends, or cutting can take place by bringing together the forceps arms, and moving the forceps as a unit sideways, using the outer vertices 39 opposite to that of the vertices 40, or downward using the vertices 42 at the bottom. This gives the surgeon complete freedom as to how he or she can use the electrode during a procedure. The triangles are sharp enough to allow cutting or blunt dissection without electrosurgical currents, but in most situations electrosurgical currents will be applied at the same time as cutting to enhance the cutting and achieve hemostasis.

Figure 4B:
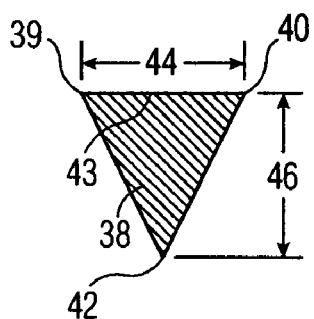
Figure 4C:
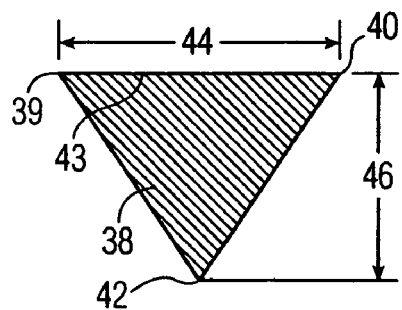

An important feature is the dimensions of the unipolar forceps of the invention. Preferably, it comes as a family in two different lengths for different breast procedures each with different sized working ends. Preferably, the overall length measured from the working end tip to the fittings 34 for one member of the family of electrodes is about 230 mm, and for the other member is about 210 mm. The former is mainly for inframammary approaches and the latter for periareolar approaches. While having both suction/fluid tubings are preferred, it is also possible to omit the fluid tubing for the shorter version for the periareolar approach. The working ends 36 also preferably come in three sizes illustrated at FIGS. 4A, 4B, and 4C. The smallest preferably has a transverse dimension 44 of about 1.8 mm and a height 46 of about 1.36 mm. The next largest preferably has a transverse dimension 44 also of about 1.8 mm but a larger height 46 of about 1.8 mm. The largest preferably has a transverse dimension 44 of about 3 mm and a height 46 of about 2.26 mm. The different sized forceps and working ends are useful for surgical procedures on different sized breasts and for different procedures.

In all cases, the complete forceps is completely insulated except for the small bare working end, which is bare from the line 48 to the tip.

In use of the forceps of the invention, with a suction source attached to the tubing 30, when the suction generator is activated, the reduced pressure is conveyed down the hollow tubing 22, and escapes via the ports 26 and 28 at the exit of the tubing 22, which it will be noted is always located very close to the point of origin of the smoke plume, which is where the working electrode end 36 excises the tissue when the electrosurgical apparatus is activated. This allows smoke and airborne contaminants to be captured close to their point of origin, and avoids the need of an additional staff member to hold a separate plume capture device near the excision site. The close proximity of the capture ports 26, 28 to the plume origin also allows the use of lower reduced pressure and thus lower noise levels. Similarly, when a fluid source is connected to the fitting 32 and activated, irrigating fluid such as saline solution will exit from the port 26 again close to the excision site.

As a result of the relatively simple construction, manufacture is quite simple and low cost, which is important for disposable hospital and office environments.

When RF energy is supplied, it will flow to the sharp vertices of the working end. The RF energy focuses on the sharp corners of the forceps' tip. The RF energy flowing through the sharp edge of the working end allows for dissection and excision of all degrees of breast tissue types, while at the same time effectively coagulating any bleeders that may result.

The RF forceps of the invention enables the surgeon to use one instrument to provide the necessary surgical features of cutting, coagulation and suction, with or without suction or fluids, with RF energy being applied during part or all of the time that the dissection procedure is carried out, with RF energy and blunt dissection, or with blunt dissection, or with suction alone without RF energy being applied. The surgeon would be otherwise required to utilize several different surgical instruments to accomplish what the RF forceps probe alone can accomplish. The changing of instruments during the surgical intervention prolongs the surgery, blood loss and anesthetic time for the patient.

By interfacing the RF breast probe with the ultra-high 3.8–4.0 MHz Radiosurgery apparatus, a number of surgical and clinical advantages, namely: better operative results, due to the high frequency radiosurgery device's ability to significantly reduce tissue necrosis; minimal scarring; reduced surgical pain and post-operative pain; and controlled bleeding and post-operative bleeding.

Precise 3.8–4.0 MHz high frequency/low temperature dissection, using the special monopolar plume suction forceps to cut and coagulate bleeding vessels under direct vision can produce a very precise pocket in short time (less than 20–30 min.). The radiofrequency method dramatically reduces the risk of complications (bleeding, infection, asymmetry, etc). Additionally typically there is less pain and a shorter recovery period.

Other variations in the shape of the electrosurgical electrode working end while retaining its benefits and advantages will be evident to those skilled in the art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical unipolar electrode in the form of forceps for breast tissue surgery, comprising:
   a) an elongated body extending in a longitudinal direction and comprising first and second arms connected at a first end for removably attaching to electrosurgical apparatus and laterally spaced apart at a second end, the first and second arms having inner surfaces facing one another,
   b) each of said first and second arms having at their second end an active electrosurgical bare end capable of supplying electrosurgical currents to tissue when the electrode is connected to electrosurgical apparatus and the latter activated,
   c) the electrosurgical bare end of each of the arms comprising a metal end having a triangular cross-section with first vertices of the triangular metal ends located on the outside of each of the bare ends and forming opposed sharp edges extending forwardly in the longitudinal direction of the elongated body such that the sharp edges of the elongated body can cut or dissect tissue when both arms are moved laterally,
   d) the remainder of the body back of the bare ends having a protective electrically-insulating surface,
   e) a first tubular member mounted on the inner surface of the first arm and extending near to the active electrosurgical end of the first arm and terminating in an open port at that end,
   f) means connected to the first arm for supplying suction to the first tubular member.

2. An electrosurgical electrode as set forth in claim 1, wherein the triangular cross-section of the electrosurgical bare end of each of the arms comprises second vertices of the triangular metal ends facing each other.

3. An electrosurgical electrode as set forth in claim 1, wherein each of triangular metal ends is oriented such that the second vertices lie in the same plane, and such that the second vertices form cutting edges when the arms are brought together.

4. An electrosurgical electrode as set forth in claim 1, wherein the open port at the end of the first tubular member is located on the inside of the first arm before the first vertices of the triangular metal ends is reached.

5. An electrosurgical electrode as set forth in claim 1, further comprising electrical connector means at the first end of the elongated body for connection to the electrosurgical apparatus, the electrical connection means being electrically connected to the first and second arms, the means for supplying suction comprising a first fitting for a suction tube mounted to the outside of the first arm before the electrical connection means and extending obliquely to the elongated direction and connected to the first tubular member.

6. An electrosurgical electrode as set forth in claim 5, further comprising a second tubular member mounted on the inner surface of the second arm and extending near to the active electrosurgical end of the first arm and terminating in an open port at that end located on the inside of the second arm before the first vertices of the triangular metal ends is reached.

7. An electrosurgical electrode as set forth in claim 6, further comprising a second fitting for an irrigation tube mounted to the outside of the second arm before the electrical connection means and extending obliquely to the elongated direction and connected to the second tubular member.

8. An electrosurgical electrode as set forth in claim 1, wherein the first tubular member has two spaced openings at its end.

9. An electrosurgical electrode as set forth in claim 1, wherein the overall length of the body is about 230–210 mm.

10. An electrosurgical electrode as set forth in claim 1, wherein the triangular metal end has a side length of about 1.8–3 mm, and a height of about 1.3–2.3 mm.

11. In combination:
   i) an electrosurgical unipolar electrode in the form of forceps for breast tissue surgery, comprising:
      a) an elongated body extending in a longitudinal direction and comprising first and second arms connected at a first end for removably attaching to electrosurgical apparatus and laterally spaced apart at a second end, the first and second arms having inner surfaces facing one another,
      b) each of said first and second arms having at their second end an active electrosurgical bare end capable of supplying electrosurgical currents to tissue when the electrode is connected to electrosurgical apparatus and the latter activated,
      c) the electrosurgical bare end of each of the arms comprising a metal end having a triangular cross-section with first vertices of the triangular metal ends located on the outside of each of the bare ends and forming opposed sharp edges extending forwardly in the longitudinal direction of the elongated body such that the sharp edges of the elongated body can cut or dissect tissue when both arms are moved laterally,
      d) the remainder of the body back of the bare ends having a protective electrically-insulating surface,
      e) a first tubular member mounted on the inner surface of the first arm and extending near to the active electrosurgical end of the first arm and terminating in an open port at that end,
      f) means connected to the first arm for supplying suction to the first tubular member,
   ii) means connected to the first arm for supplying suction to the first tubular member,
   iii) electrosurgical apparatus capable of supplying unipolar RF electrosurgical currents at a frequency of about 3.8–4 MHz, iv) electrical means connecting the electrosurgical electrode to the electrosurgical apparatus for conveying unipolar electrosurgical currents to the electrosurgical bare ends.

12. A procedure for breast reconstruction, comprising:
(i) providing an electrosurgical unipolar electrode electrode in the form of forceps for breast tissue surgery, comprising:
  a) an elongated body extending in a longitudinal direction and comprising first and second arms connected at a first end for removably attaching to electrosurgical apparatus and laterally spaced apart at a second end, the first and second arms having inner surfaces facing one another,
  b) each of said first and second arms having at their second end an active electrosurgical bare end capable of supplying electrosurgical currents to tissue when the electrode is connected to electrosurgical apparatus and the latter activated,
  c) the electrosurgical bare end of each of the arms comprising a metal end having a triangular cross-section with first vertices of the triangular metal ends located on the outside of each of the bare ends and forming opposed sharp edges extending forwardly in the longitudinal direction of the elongated body such that the sharp edges of the elongated body can cut or dissect tissue when both arms are moved laterally,
  d) the remainder of the body back of the bare ends having a protective electrically-insulating surface,
  e) a first tubular member mounted on the inner surface of the first arm and extending near to the active electrosurgical end of the first arm and terminating in an open port at that end,
  f) means connected to the first arm for supplying suction to the first tubular member,
(ii) excising breast tissue by applying the electrosurgical bare ends to the tissue while the arms are together and moving the electrode sideways.

13. A procedure for breast reconstruction as set forth in claim 12, wherein unipolar electrosurgical currents are applied to the electrosurgical bare ends during at least part of the time that step (ii) is carried out.

14. A procedure for breast reconstruction as set forth in claim 12, wherein the electrosurgical electrode incorporates means for supplying suction or fluid to the electrosurgical bare ends, and suction or fluid is applied to the electrosurgical bare ends while electrosurgical currents are applied to the electrosurgical bare ends during at least part of the time that step (ii) is carried out.

15. A procedure for breast reconstruction as set forth in claim 12, further comprising a source of electrosurgical currents having a frequency in the range of about 3.8–4.0 MHz, wherein the electrosurgical currents are applied to the electrosurgical bare ends during at least part of the time that step (ii) is carried out.

16. A procedure for breast reconstruction as set forth in claim 12, wherein the electrosurgical electrode further comprises a second tubular member mounted on the inner surface of the second arm and extending near to the active electrosurgical end of the second arm and terminating in an open port at that end,
  further comprising the steps of supplying suction to the first tubular member while electrosurgical currents are applied to the electrosurgical bare ends during at least part of the time that step (ii) is carried out, and supplying fluid to the second tubular member while electrosurgical currents are applied to the electrosurgical bare ends during at least part of the time that step (ii) is carried out.

* * * * *